(12) United States Patent
Seo et al.

(10) Patent No.: US 6,874,350 B2
(45) Date of Patent: Apr. 5, 2005

(54) APPARATUS AND METHOD FOR TESTING MECHANICAL ENDURANCE OF A SURFACE OF AN OPTICAL DISC

(75) Inventors: Hun Seo, Yongin-si (KR); Jin Hong Kim, Yongin-si (KR); Chang Ho Lee, Goyang-si (KR); Tae Hee Jeong, Seongnam-si (KR); Keum Cheol Kwak, Seoul (KR)

(73) Assignee: LG Electronics Inc., Seoul (KR)

(*) Notice: Subject to any disclaimer, the term of this patent is extended or adjusted under 35 U.S.C. 154(b) by 0 days.

(21) Appl. No.: 10/652,190

(22) Filed: Sep. 2, 2003

(65) Prior Publication Data

US 2004/0182169 A1 Sep. 23, 2004

(30) Foreign Application Priority Data

Mar. 17, 2003 (KR) ................... 10-2003-0016513

(51) Int. Cl.$^7$ ................................. G01N 3/56
(52) U.S. Cl. ............................. 73/7; 73/150 R
(58) Field of Search ................... 73/7, 150 R, 78; 204/192.13, 192.16, 192.26

(56) References Cited

U.S. PATENT DOCUMENTS

| | | | | |
|---|---|---|---|---|
| 4,958,511 A | * | 9/1990 | Marcus | 73/7 |
| 5,074,983 A | * | 12/1991 | Eltoukhy et al. | 73/150 R |
| 5,557,039 A | * | 9/1996 | Annis et al. | 73/7 |

* cited by examiner

Primary Examiner—Edward Lefkowitz
Assistant Examiner—T Miller
(74) Attorney, Agent, or Firm—Harness, Dickey & Pierce, P.L.C.

(57) ABSTRACT

An apparatus and method for testing mechanical endurance of a surface of an optical disc are disclosed. The apparatus includes a rotating plate, on which an optical disc to be scratched is loaded, for rotating the loaded optical disc, and a plurality of abrasion wheels of a predetermined type, disposed at a perpendicular to the rotating plate, for contacting the optical disc and generating the scratch, the scratch being generated when the optical disc rotates a predetermined number of turns, e.g., a maximum of 5 turns for the abrasion wheels to apply a predetermined load on the optical disc.

18 Claims, 3 Drawing Sheets

APPARATUS AND METHOD FOR TESTING MECHANICAL ENDURANCE OF A SURFACE OF AN OPTICAL DISC

This application claims the benefit of the Korean Application No. P2003-16513 filed on Mar. 17, 2003, which is hereby incorporated by reference.

BACKGROUND OF THE INVENTION

1. Field of the Invention

The present invention relates to an apparatus and method for testing quality of an optical disc, and more particularly, to an apparatus method for testing quality of mechanical endurance of a surface of an optical disc.

2. Discussion of the Related Art

Up to now, there are recording media such as a magnetic recording tape, a laser disc (LD) or a compact disc (CD) as an optical disc, and a digital video disc (DVD) newly born with a vast recording capacity.

Since the optical disc among the recording media utilizes a digital recording system different from the conventional recording system, that is, magnetic recording system, and has a very small volume and weight so that it is efficient and convenient to keep and carry, it is a recent trend for a consumer to prefer the optical disc.

However, even any appliance should be used without any defect, and if there were any problem in quality, then the consumer's reliability for the manufacturer would be decreased.

This causes more serious problem in the optical disc having minute signal characteristics and brings inferior quality originated from the error of thickness of a disc, scratch, deformity, fingerprint, and attachment of foreign material during manufacturing of the product.

Thus, a produced optical disc undergoes the quality test as a next process, and the optical disc is shipped to an optical disc market.

A conventional quality test for an optical disc is generally performed by four measuring drives.

First, under the assumption that characteristics of optical discs manufactured by the same equipment are identical, the manufacturer makes a choice of an arbitrary optical disc from all of the manufactured optical discs and loads the selected optical disc onto a measuring system.

In the first measuring drive, a high frequency wave signal and a jitter are measured by means of a signal reproduced from the optical disc.

In the second measuring drive, a servo signal (a focusing error signal and a tracking error signal) are measured based on a signal reproduced from the optical disc.

In the third measuring drive, the mechanical characteristics of the optical disc, which undergoes the quality test, are measured.

Finally, in the fourth measuring drive, the optical characteristics of the optical disc are measured.

As described above, according to the conventional test, an accuracy of information recording, and the mechanical characteristics and an optical characteristics of the optical disc are inspected.

From these, since a mechanical damage that would occur on an incident surface of an information recording/reproducing laser beam during the use of an high density optical disc, that is, a scratch and the like causes the deterioration of a signal of an optical disc as well as data loss, and in more worse case, brings the recording and/or reproducing of information onto the optical disc impossible, the damage takes the most important portion of the quality test of the optical disc.

Therefor, to prevent this, a protective coating may be formed to enhance the mechanical stiffness or hardness of the surface of the optical disc.

However, after forming the protective coating on the disc surface for this purpose, the mechanical characteristics of the protective coating should be quantized. Namely, there is need to quantize for how long the protective coating endure the scratch which would occur during the use of the optical disc.

There are a pencil hardness test and a taber abrasion test as a test for the quantization of surface-proof of the high-density optical disc.

The pencil hardness test is an estimating method for estimating the scratch at a hardness value corresponding a hardness of the pencil at an instant when the scratch occurs by contacting pencils of which different hardness to the optical disc in a rectilinear motion.

However, the pencil hardness test is a test for generating the scratch by which a human contacts the pencil on the surface of the optical disc, has disadvantages that it is difficult not only to maintain same load continuously, but also to generate the quantization scratch because the scratch does not occur as many as desired.

The taber abrasion test is a test to estimate degree of endurance by uniformly wearing the surface of the optical disc while giving a predetermined load by means of D1004 method of a standard, American Society for Testing and Materials (ASTM) as a kind of an abrasion wheel.

In the conventional taber abrasion testing apparatus, if an optical disc to be scratched is loaded and rotated, a plurality of abrasion wheels having a predetermined weight contact the optical disc at a perpendicular position to the optical disc so that scratch the surface of the optical disc by a uniform load for at least more ten rotation of the optical disc.

At that time, the ASTM defines the load generated from the abrasion wheel less than 9.8 N (1000 gf), and there are several kinds such as CS-10F, CS-10, and CS-17 to be used.

The taber abrasion testing apparatus as described above is an equipment designed for the purpose of not testing the mechanical endurance of the surface of the optical disc by scratching the optical disc, but testing a degree of the scratch of general plastic goods.

Therefore, the scratch occurring by the taber abrasion testing apparatus is remarkably different from the scratch generated when the optical disc is used actually in real life.

Namely, the taber abrasion testing apparatus determines the endurance of the surface of the optical disc by wearing the surface. This is remarkably different from the situation that real-generated scratch is reacted in a drive (for example, an optical disc drive) for driving the optical disc by responding the operation.

Therefore, since the manufacturer determines the quality of the optical disc by his relative determination with his veteran know-how not quantitative classification according to an actual reference standard when to determine the quality of the optical disc poor or good by the taber abrasion testing apparatus, there are a plenty of errors. Moreover, since the scratches generated on the optical disc in real life and by the taber abrasion testing apparatus are different from each other in the shape, a try to determine the optical disc poor or good with only the know-how without absolute reference value makes vast of errors.

As described above, since, up to now, there is not a special method for quantizing generation degree of the scratch in order to test the mechanical endurance of the surface of the optical disc, a quantization of the degree of the scratch is urgently demanded.

SUMMARY OF THE INVENTION

Accordingly, the present invention is directed to an apparatus and method for testing mechanical endurance of a surface of an optical disc that substantially obviates one or more problems due to limitations and disadvantages of the related art.

An object of the present invention is to provide an optimum apparatus for testing to quantize characteristics of mechanical endurance of a surface of an optical disc for the purpose of enhancing mechanical characteristics of the surface and a method performed by the apparatus.

Another object of the present invention is to provide an apparatus for testing mechanical endurance of a surface of an optical disc, increasing reliability, and saving the testing cost, and a method performed by the apparatus.

Still another object of the present invention is to provide an apparatus for classifying a poor product and a good product by setting an absolute reference rapidly and precisely, and a method performed by the apparatus.

Still another object of the present invention is to generate scratch of the closest type of the scratch to be generated in real life so as to enhance the reliability of the test for the mechanical endurance of a surface of an optical disc.

Additional advantages, objects, and features of the invention will be set forth in part in the description which follows and in part will become apparent to those having ordinary skill in the art upon examination of the following or may be learned from practice of the invention. The objectives and other advantages of the invention may be realized and attained by the structure particularly pointed out in the written description and claims hereof as well as the appended drawings.

To achieve these objects and other advantages and in accordance with the purpose of the invention, as embodied and broadly described herein, an apparatus for testing mechanical endurance of a surface of an optical disc, includes a rotating plate, on which an optical disc to be scratched is loaded, for rotating the loaded optical disc, and a plurality of abrasion wheels, disposed at a perpendicular to the rotating plate, for contacting the optical disc and generating the scratch, the scratch being generated when the optical disc rotates a predetermined number of turns, e.g., a maximum of 5 turns, for the abrasion wheels to apply a predetermined load on the optical disc.

In another aspect of the present invention, the load applied on the optical disc by the abrasion wheels ranged from 0.5 N (50 gf) to 16.2 N (1650 gf) and the depth of the scratch on the surface of the optical disc ranges 0 $\mu$m to 2 $\mu$m.

The abrasion wheel may be selected any one of CS-10F, CS-10, and CS-17.

The scratch may be generated when the optical disc rotates a predetermined turn, e.g., one turn for the optical disc is applied with a load of 0.5 N to 2.5 N (50 gf to 250 gf) by the CS-10F abrasion wheel, when the optical disc rotates a predetermined turn, e.g., one turn for the optical disc is applied with a load of 6.4 N to 8.3 N (650 gf to 850 gf) by the CS-10 abrasion wheel, and when the optical disc rotates a predetermined turn, e.g., one turn for the optical disc is applied with a load of 11.8 N to 13.7 N (1200 gf to 1400 gf) by the CS-17 abrasion wheel.

In still another aspect of the present invention, a method of testing a mechanical endurance of a surface of an optical disc by using a test apparatus of which a rotating plate rotates the optical disc and a plurality of abrasion wheels generates scratch on the optical disc, includes the steps of fixing the optical disc on the rotating plate, rotating the optical disc by the rotating plate, contacting the abrasion wheels to the surface of the optical disc and increasing a contacting load of the abrasion wheels and the optical disc by a predetermined load, generating the scratch on the surface of the optical disc by maintaining the contacting load of the optical disc and the abrasion wheels until the optical disc rotates a predetermined number of turns, e.g., less than five turns, and departing the abrasion wheels contacting the optical disc from the optical disc, and separating the optical disc from the rotating plate and determining whether the optical disc is poor or good by comparing a result of the scratch generated on the surface of the optical disc with a predetermined reference value.

According an aspect of the present invention, the optical disc determining step determines that the optical disc is good when the depth of the scratch generated on the surface of the optical disc is equal to or greater than 0 $\mu$m or less than 2 $\mu$m, and that the optical disc is poor when the depth of the scratch generated on the surface of the optical disc is greater than 2 $\mu$m.

The absolute reference value for determining the optical disc poor or good is set to 2 $\mu$m.

It is to be understood that both the foregoing general description and the following detailed description of the present invention are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this application, illustrate embodiment(s) of the invention and together with the description serve to explain the principle of the invention. In the drawings.

DETAILED DESCRIPTION OF THE INVENTION

Reference will now be made in detail to the preferred embodiments of the present invention, examples of which are illustrated in the accompanying drawings. Wherever possible, the same reference numbers will be used throughout the drawings to refer to the same or like parts.

Figure 1:
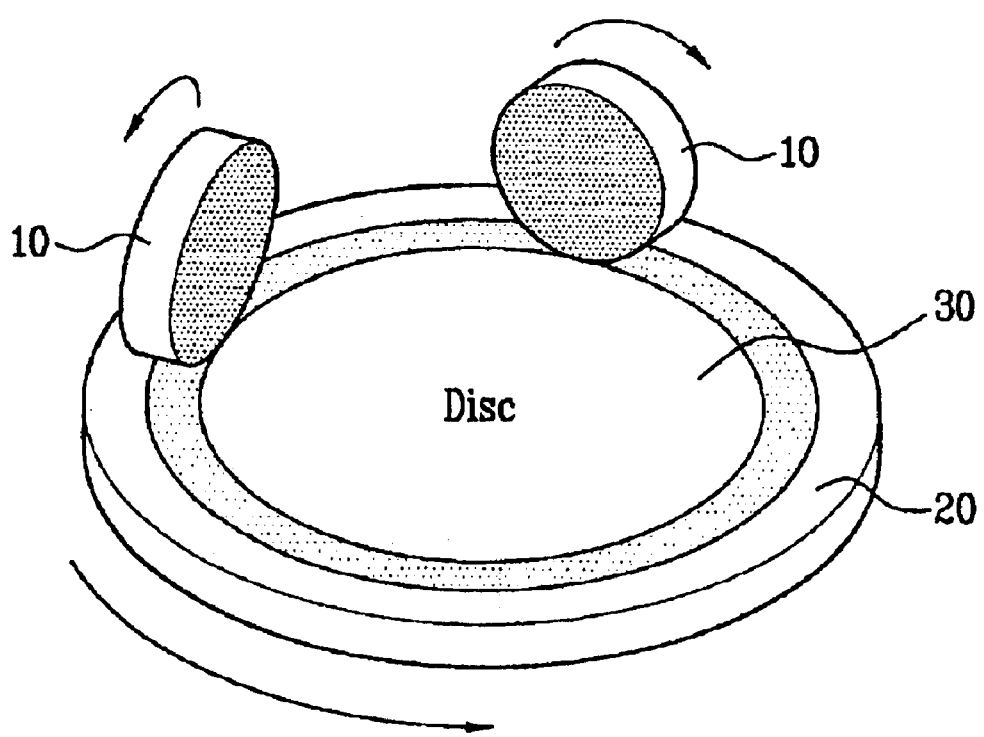
FIG. 1 illustrates a schematic view showing a taber abrasion testing apparatus according to the present invention.

FIG. 1 illustrates a schematic view showing a taber abrasion testing apparatus according to the present invention.

As illustrated in FIG. 1, an apparatus for testing mechanical endurance of a surface of an optical disc includes a rotating plate 20, on which an optical disc 30 to be scratched is loaded, for rotating the loaded optical disc 30, and a plurality of abrasion wheels 10, disposed at a perpendicular to the rotating plate 20, for contacting the optical disc 30 and generating the scratch, the scratch being generated when the optical disc 30 rotates under 5 turns for the abrasion wheels 10 apply a predetermined load on the optical disc 30. One abrasion wheel rotates to reverse direction with respect to the other abrasion wheel.

As a result, the apparatus determines whether the optical disc has a predetermined endurance by comparing a result from the scratch generated on the surface of the optical disc with a predetermined reference value.

Meanwhile, the abrasion wheels are selected from any one of CS-10F, CS-10, and CS-17.

Hereinafter, the testing method of the mechanical endurance of the surface of the optical disc of the present invention by reference with the accompanying drawings.

Figure 2:
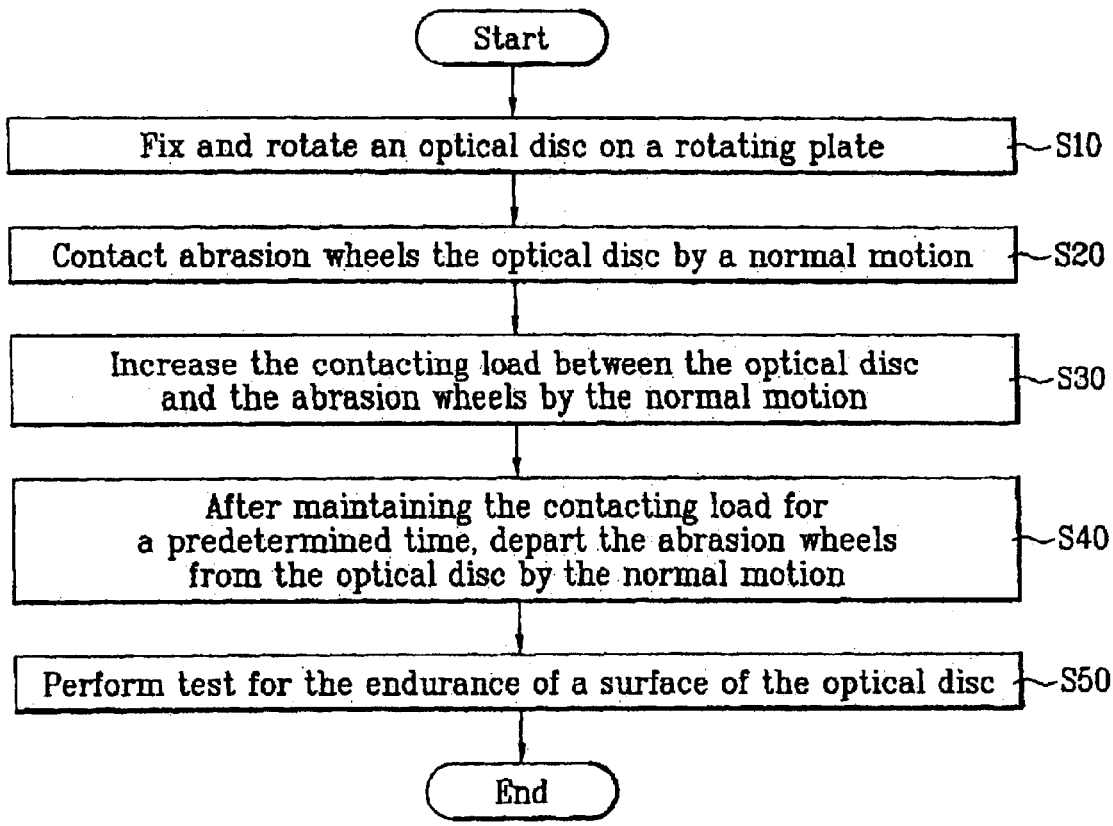
FIG. 2 illustrates a flowchart showing a method of testing mechanical endurance of a surface of an optical disc according to the present invention.

FIG. 2 illustrates a flowchart showing a method of testing mechanical endurance of a surface of an optical disc according to the present invention.

As shown in FIG. 2, first, the optical disc 30 is fixed on the rotating plate 20, and then the rotating plate 20 rotates together the optical disc (Step S10).

Next, the abrasion wheels 10 contact the optical disc 30 being rotated at an upper end in a normal motion (Step S20).

The predetermined load is applied on the optical disc 30 in normal direction according to the scratch test so that the contacting load between the optical disc 30 and the abrasion wheels 10 is increased (Step S30).

After maintaining the contacting load between the optical disc 30 and the abrasion wheels 10 as many as the predetermined turns of the optical disc 30, the abrasion wheels 10 are moved in the normal direction so that the abrasion wheels are departed from the optical disc 30 (Step S40).

Figure 3:
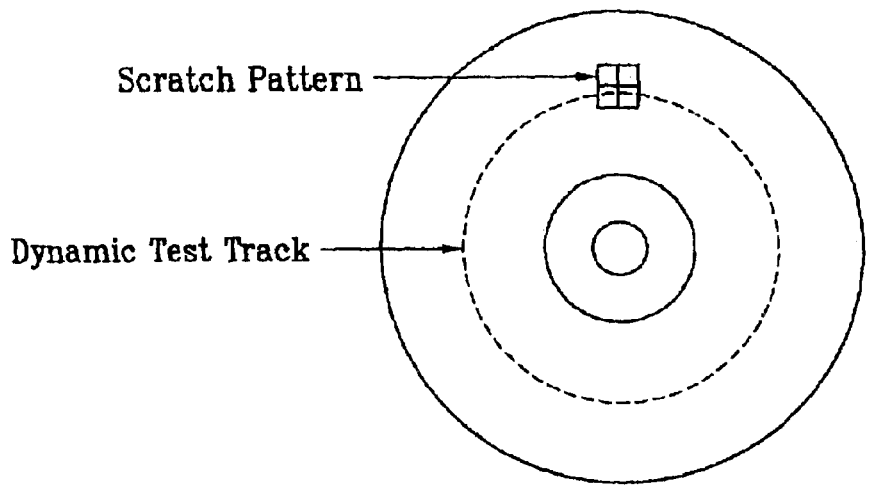
FIG. 3 illustrates a view explaining a predetermined scratch pattern is generated on an optical disc by using a micro-scratch tester according to the present invention.

As described above, on the surface of the optical disc 30 being rotated, the predetermined load and the abrasion wheels 10 contacting the optical disc 30 based on the predetermined turns cause the generation of a predetermined scratch pattern on the surface of the optical disc 30 as illustrated in FIG. 3.

As illustrated in FIG. 3, by using the taber abrasion tester according to the present invention, the predetermined scratch pattern is generated on the surface of the optical disc 30, so that the depth of the scratch can be obtained.

Figure 4:
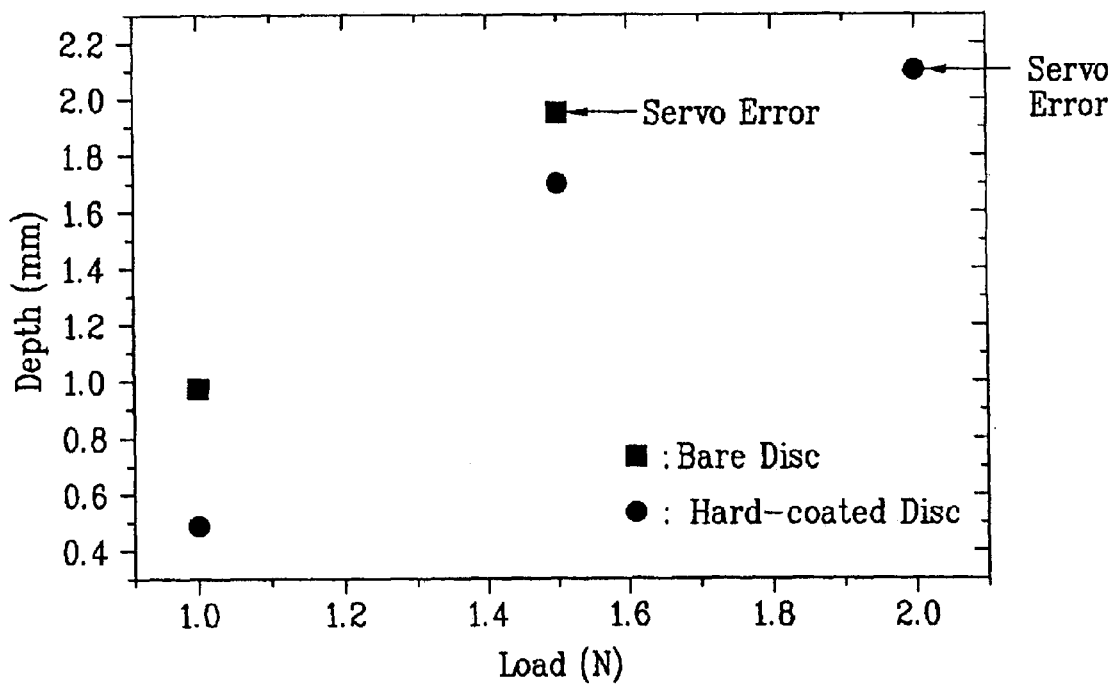
FIG. 4 illustrates a graph showing experimental values of scratch depth generated according to pressure applied on an optical disc according to the present invention.

FIG. 4 illustrates a graph showing experimental values of the scratch depth generated according to pressure applied on the optical disc 30 according to the present invention. Here, a bare disc without a coating layer and a hard-coated disc are used as experimental materials.

In the experiment as illustrated in FIG. 4, if the scratch with depth deeper than 2 $\mu$m is generated, it is measure that a servo error is generated when a dynamic characteristics of the optical disc 30 is estimated.

Namely, when the endurance test of the surface of the optical disc 30 is performed, the 2 $\mu$m is defined as the absolute reference value for determining whether the optical disc 30 is poor or good, and by finding a still wool test condition causing the scratch depth of 2 $\mu$m, the mechanical endurance of the surface of the optical disc 30 under the condition so that the generation degree of the scratch is quantized.

Figure 5:
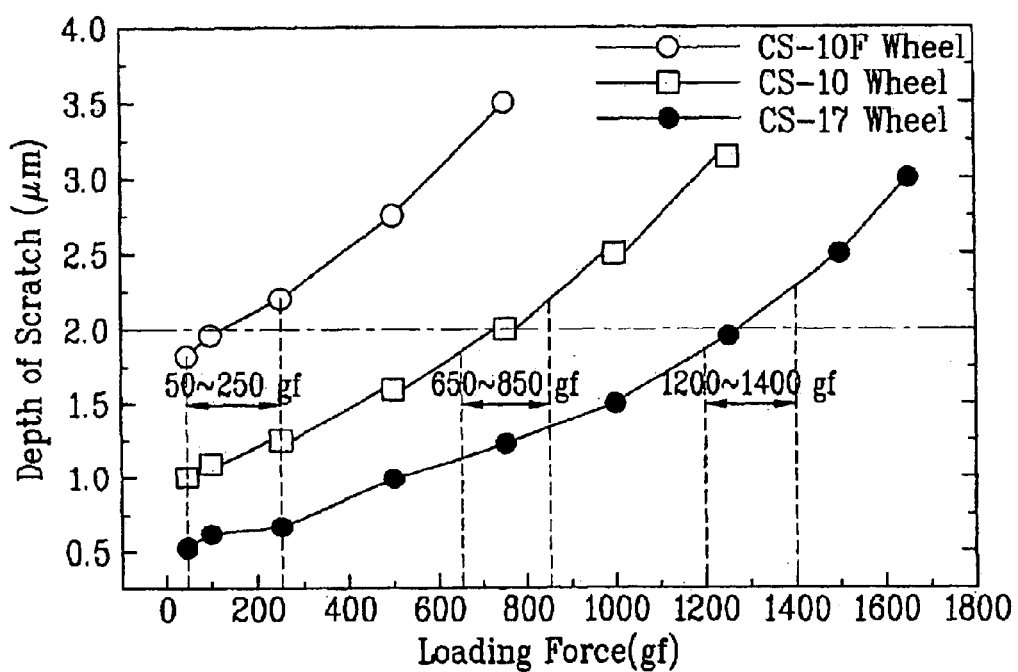
FIG. 5 illustrates a graph explaining a method of testing mechanical endurance of a surface of an optical disc according to the present invention.

FIG. 5 is a graph explaining a method of testing mechanical endurance of a surface of an optical disc according to the present invention, and represents a graph as the depth of the scratch generated on the optical disc 30 by the load applied to kind of abrasion wheel such as CS-10F, CS-10, and CS-17.

As illustrated in FIG. 5, the load generated from the abrasion wheels 10 is quantized to 0.5 N (50 gf) to 16.2 N (1650 gf), and is differently set according to kind of the abrasion wheels.

Namely, in the taber abrasion test, under the condition of using the CS-10F as the abrasion wheel 10 and rotating the optical disc 30 only one turn, it is understood that the load generating the scratch depth of 2 $\mu$m ranges 0.5 N (50 gf) to 2.5 N (250 gf), preferably 1.5 N (150 gf).

Under the condition of using the CS-10 as the abrasion wheel 10 and rotating the optical disc 30 only one turn, it is understood that the load generating the scratch depth of 2 $\mu$m ranges 6.4 N (650 gf) to 8.3 N (850 gf), more preferably 7.4 N (750 gf).

Moreover, under the condition of using the CS-17 as the abrasion wheel 10 and rotating the optical disc 30 only one turn, it is understood that the load generating the scratch depth of 2 $\mu$m ranges 11.8 N (1200 gf) to 13.7 N (1400 gf), more preferably 13.2 N (1350 gf).

Therefore, if the abrasion wheel 10 were hard one, namely, CS-10F, the load of the surface of the optical disc 30 is quantized to 0.5 N (50 gf) to 2.5 N (250 gf), more preferably quantized to 1.5 N (150 gf), if the abrasion wheel 10 were middle one, namely, CS-10, the load of the surface of the optical disc 30 is quntized to 6.4 N (650 gf) to 8.3 N (850 gf), more preferably quantized to 7.4 N (750 gf), and if the abrasion wheel 10 were soft one, namely, CS-17, the load of the surface of the optical disc 30 is quntized to 11.8 N (1200 gf) to 13.7 N (1400 gf), more preferably quantized to 13.2 N (1350 gf).

The contacting load between the optical disc 30 and the abrasion wheel 10 is maintained to a corresponding load in proportion to numbers of the turn of the optical disc according to quantized condition so that the scratch is generated on the optical disc 30.

At that time, by reducing the abrasion degree of the optical disc 30 due to the abrasion wheel 10 at minimum by decreasing the number of the turn of the optical disc 30 to under 5 turns, the scratch very closer to the scratch to be generated in an actual life so that the reliability of test for the mechanical endurance of the surface of the optical disc 30 can be enhanced.

In other words, the scratch on the optical disc 20 in the real life is generated by being scratched few times, on the contrary, the more times the abrasion wheels 10 are scratched, the more the scratch during several rotation of the optical disc 30 by using the taber abrasion tester makes a difference from the scratch in real life due to abrasion of ambient optical disc to be scratched.

With this reason, there is a problem in the reliability for the mechanical endurance test of the surface of the optical disc due to the scratch, and then this is the worst serious problem occurring in the mechanical endurance test of the surface of the optical disc according to the conventional art.

According to the present invention, since the number of turns of the optical disc can be reduced to 1 turn at minimum to 5 turns at maximum value by the quantized-absolute reference value, the reliability of the mechanical endurance test of the surface of the optical disc can be enhanced by causing the scratch of type the closest the scratch in real life.

As described above, just during one turn of the optical disc, after generating the scratch by using the load condition 0.5 N (50 gf) to 16.2 N (1650 gf) causing the scratch with a depth of 2 µm, the endurance is to be tested through the scratch generated on the surface of the optical disc 30 by separating the scratched disc 30 from the rotating plate 20. Next, the optical disc 30 is determined to be poor or good (Step S50).

After this, other optical disc to be tested is loaded on the rotating plate 20, the testing operations as described above are repeated so that a plenty of optical discs are determined to be poor or good.

As described above, the apparatus for testing the mechanical endurance of the surface of the optical disc and the method performed the apparatus have following advantages.

First, the generation degree of the scratch is quantized to enhance the mechanical characteristics of the surface so that the preservation of data according to achievement for the high-density of the optical disc can be increased.

Second, since the quality of the optical disc is tested easily and precisely, the reliability of the optical disc can be enhanced.

Third, the scratch can be formed as much as to wish in a short time so that the testing time for the mechanical endurance test of the surface of the optical disc can be also decreased and the manufacturing cost may be reduced.

It will be apparent to those skilled in the art that various modifications and variations can be made in the present invention. Thus, it is intended that the present invention covers the modifications and variations of this invention provided they come within the scope of the appended claims and their equivalents.

What is claimed is:

1. An apparatus for testing mechanical endurance of a surface of an optical disc, comprising:
   a rotating plate, on which an optical disc to be scratched is loaded, for rotating the loaded optical disc; and
   a plurality of abrasion wheels, for contacting the optical disc and generating the scratch, the scratch being generated when the optical disc rotates a predetermined number of turns and the abrasion wheels apply a predetermined load on the rotated optical disc,
   wherein the apparatus determines whether the optical disc has a predetermined endurance by comparing a result from the scratch generated on the surface of the optical disc with a predetermined reference value.

2. The apparatus of claim 1, wherein the load applied on the optical disc by the abrasion wheels ranged from 0.5 N (50 gf) to 16.2 N (1650 gf).

3. The apparatus of claim 1, wherein a depth of the scratch on the surface of the optical disc ranges from 0 µm to 2 µm.

4. The apparatus of claim 1, wherein the abrasion wheel is any one of CS-10F, CS-10, and CS-17.

5. The apparatus of claim 1, wherein the scratch is generated when the optical disc rotates the predetermined number of turns and the rotated optical disc is applied with a load of 0.5 N to 2.5 N (50 gf to 250 gf) by the CS-10F abrasion wheel.

6. The apparatus of claim 1, wherein the scratch is generated when the optical disc rotates the predetermined number of turns and the rotated optical disc is applied with a load of 6.4 N to 8.3 N (650 gf to 850 gf) by the CS-10 abrasion wheel.

7. The apparatus of claim 1, wherein the scratch is generated when the optical disc rotates the predetermined number of turns and the rotated optical disc is applied with a load of 11.8 N to 13.7 N (1200 gf to 1400 gf) by the CS-17 abrasion wheel.

8. A method of testing mechanical endurance of a surface of an optical disc by using a testing apparatus of which a rotating plate rotates the optical disc and a plurality of abrasion wheels generates a scratch on the optical disc, comprising the steps of:
   rotating the optical disc by the rotating plate;
   contacting the abrasion wheels with a predetermined load to the surface of the optical disc;
   applying the abrasion wheels to generate the scratch on the surface of the optical disc during which the optical disc rotates a predetermined number of turns; and
   determining whether the optical disc has a predetermined endurance by comparing a result from the scratch generated on the surface of the optical disc with a predetermined reference value.

9. The method of claim 8, wherein the load applied on the optical disc by the abrasion wheels during the generation of the scratch ranged from 0.5 N (50 gf) to 16.2 N (1650 gf).

10. The method of claim 8, wherein the determining step compares a depth of the scratch on the surface of the optical disc with the predetermined reference value, the depth ranging from 0 µm to 2 µm.

11. The method of claim 8, wherein the abrasion wheel is any one of CS-10F, CS-10, and CS-17.

12. The method of claim 8, wherein the scratch is generated when the optical disc rotates the predetermined number of turns and the rotated optical disc is applied with a load of 0.5 N to 2.5 N (50 gf to 250 gf) by the CS-10F abrasion wheel.

13. The method of claim 8, wherein the scratch is generated when the optical disc rotates the predetermined number of turns and the rotated optical disc is applied with a load of 6.4 N to 8.3 N (650 gf to 850 gf) by the CS-10 abrasion wheel.

14. The method of claim 8, wherein the scratch is generated when the optical disc rotates the predetermined number of turns and the rotated optical disc is applied with a load of 11.8 N to 13.7 N (1200 gf to 1400 gf) by the CS-17 abrasion wheel.

15. The method of claim 8, wherein the determining step determines that the optical disc is good when a depth of the scratch generated on the surface of the optical disc is equal to or greater than 0 µm or less than 2 µm, and that the optical disc is poor when the depth of the scratch generated on the surface of the optical disc is greater than 2 µm.

16. The method of claim 8, wherein the predetermined reference value for determining the optical disc poor or good is set to 2 µm.

17. The apparatus of claim 1, wherein the types of the abrasion wheels is CS-10F, the predetermined load is 2.5 N by the CS-10F abrasion wheels, and the predetermined number of turns are 5 turns.

18. The method of claim 8, wherein the type of the abrasion wheels is CS-10F, the predetermined load is 2.5 N by the CS-10F abrasion wheels, and the predetermined number of turns is 5 turns.

* * * * *